(12) United States Patent
Lilieblad

(10) Patent No.: US 6,517,887 B1
(45) Date of Patent: Feb. 11, 2003

(54) METHOD AND A DEVICE FOR COATING A TABLET, A CAPSULE, A PILL OR THE LIKE

(76) Inventor: Fredrik Robin Lechard Lilieblad, Yngvevágen 1, Djursholm 18264 (SE)

(*) Notice: Subject to any disclaimer, the term of this patent is extended or adjusted under 35 U.S.C. 154(b) by 0 days.

(21) Appl. No.: 09/914,863
(22) PCT Filed: Mar. 1, 2000
(86) PCT No.: PCT/SE00/00406
§ 371 (c)(1),
(2), (4) Date: Sep. 4, 2001
(87) PCT Pub. No.: WO00/51569
PCT Pub. Date: Sep. 8, 2000

(30) Foreign Application Priority Data

Mar. 4, 1999 (SE) .............................................. 9900772

(51) Int. Cl.[7] .......................... A61L 27/54; B05D 1/40; B05D 1/42
(52) U.S. Cl. ...................... 427/2.14; 427/2.1; 427/346; 427/355; 427/431; 427/434.4; 427/434.7; 118/13; 118/15; 118/18; 118/26; 118/30; 118/40; 118/404; 118/423; 426/302; 426/305; 426/516; 426/122; 426/394

(58) Field of Search ................................. 427/2.1, 2.14, 427/346, 355, 431, 434.4, 434.7; 118/13, 15, 18, 26, 30, 40, 404, 423; 426/302, 305, 516, 122, 394

(56) References Cited

U.S. PATENT DOCUMENTS

| 3,938,686 A | * | 2/1976 | Milligan et al. | .......... | 15/257.05 |
| 5,228,573 A | * | 7/1993 | Pavelle et al. | ............... | 116/206 |
| 5,676,990 A | * | 10/1997 | Wawrzynski | ............... | 118/100 |
| 5,965,210 A | * | 10/1999 | Tada et al. | ................... | 118/405 |

* cited by examiner

Primary Examiner—Shrive P. Beck
Assistant Examiner—Jennifer Kolb Michener

(57) ABSTRACT

The method relates to a disposable device for the application of a coating (2) on a tablet, a capsule or a pill. The coating (2) is applied enclosing the tablet, capsule or pill (3) during its passage through a bowl formation (4) with a coating mass (5) and through an elastic diaphragm (12) located in the bottom (11) and provided with a centrally disposed, conveniently penetrable opening (13). During the passage of the tablet, capsule of pill (3) the opening (13) encloses the tablet, capsule or pill and simultaneously shapes a film of coating mass (5) thereon.

4 Claims, 2 Drawing Sheets

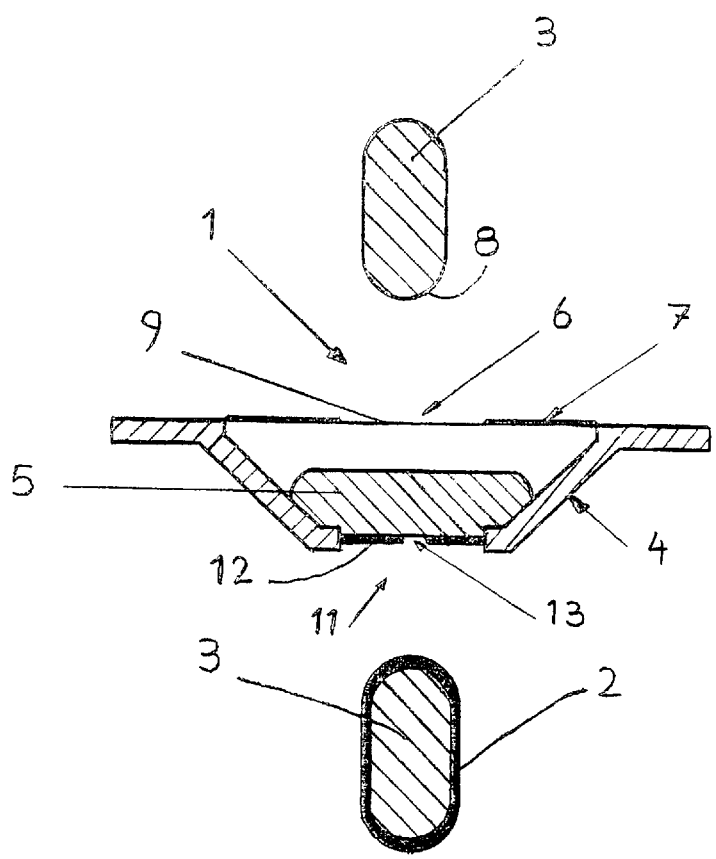
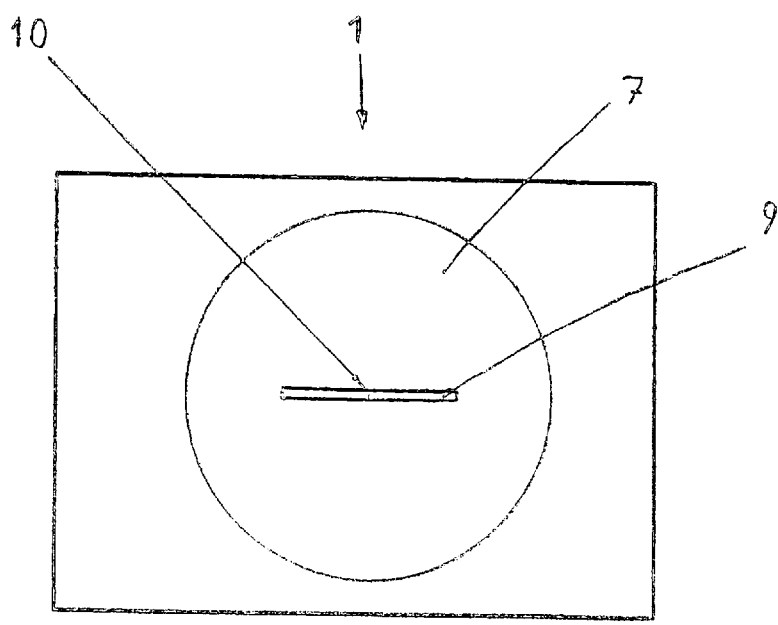

METHOD AND A DEVICE FOR COATING A TABLET, A CAPSULE, A PILL OR THE LIKE

TECHNICAL FIELD

The present invention relates to a method and to a disposable device for coating a tablet, a capsule, a pill or the like in order to improve the taste and the swallowing characteristics of the tablet.

BACKGROUND AND SUMMARY OF THE INVENTION

Many of the tablets today on the market have a rough surface and are lacking a delicate taste, which results in that many persons find it unpleasant to use the tablet at issue.

The object of the present invention is accordingly to provide a method and a disposable device by means of which a tablet, a capsule, a pill or the like can be provided with a coating which makes it easy to swallow the tablet and improves its taste involving a substantial reduction of the problems today experienced in connection with the swallowing of certain tablets.

Thanks to the invention there has now been provided a method and a disposable device for simple application of a coating on the tablet. The application of a coating mass, forming the above-mentioned coating can, with the aid of the device designed according to the invention, be carried out shortly before the swallowing of the tablet. When the tablet has been inserted in the mouth and is to be swallowed, the coating will shield off the taste of the tablet and replace it by its own taste. The saliva in the oral cavity then causes the coating to start melting slowly, for example because it contains glucose. This makes the surface of the tablet slippery which facilitates the swallowing thereof.

Accordingly, the coating will replace the taste of a given tablet with a more palatable taste chosen by the person himself. This is experienced as attractive especially by children and by other persons who find it difficult to swallow a tablet. The function of the coating is that those persons do not any longer regard a medical tablet as unpleasant since it can be associated with a positive taste experience. Also, the tablet can be given a more inviting color and shape in response to the type of coating mass used. The coating mass can be manufactured with several different tastes and may also contain vitamins. A coating according to the invention also has the advantage that it extends the time interval up to the point when the surface of the tablet starts to dissolve and unpleasant taste is experienced. The coating also makes it possible to divide the tablet into smaller sections, for example through the center, without any deterioration of the taste and the swallowing characteristics. As has been mentioned above, the swallowing characteristics become especially positive for children and persons having a swollen throat or other swallowing problems. Finally it can be mentioned that the coating does in addition thereto stimulate the secretion of saliva in the oral cavity that makes it easier to swallow the tablet, also when no beverage is available.

BRIEF DESCRIPTION OF THE DRAWINGS

Some preferred embodiments of the invention will be described below, reference being made to the drawings.

FIG. 1 is a cross-sectional view of a disposable device of the present invention.

FIG. 2 is a top view of the device shown in FIG. 1.

DETAILED DESCRIPTION

Figure 3:
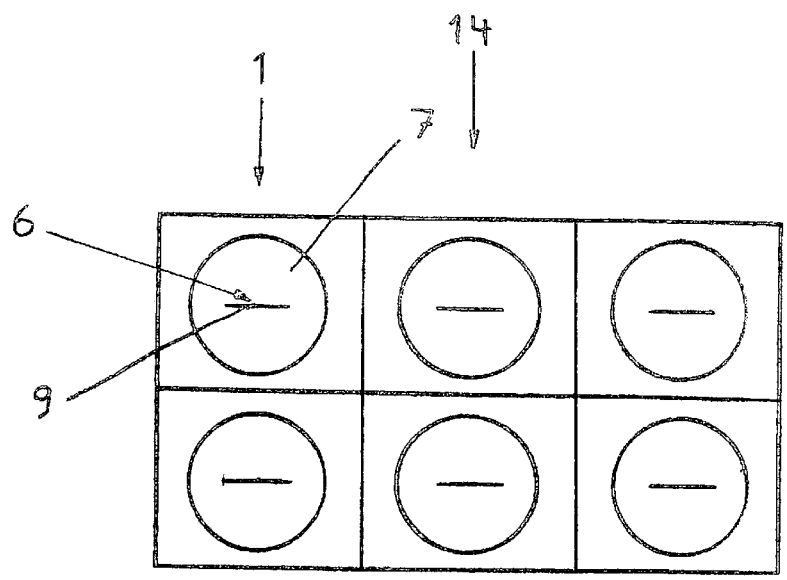
FIG. 3 is a top view of a card comprising six devices according to FIGS. 1 and 2.
Figure 4:
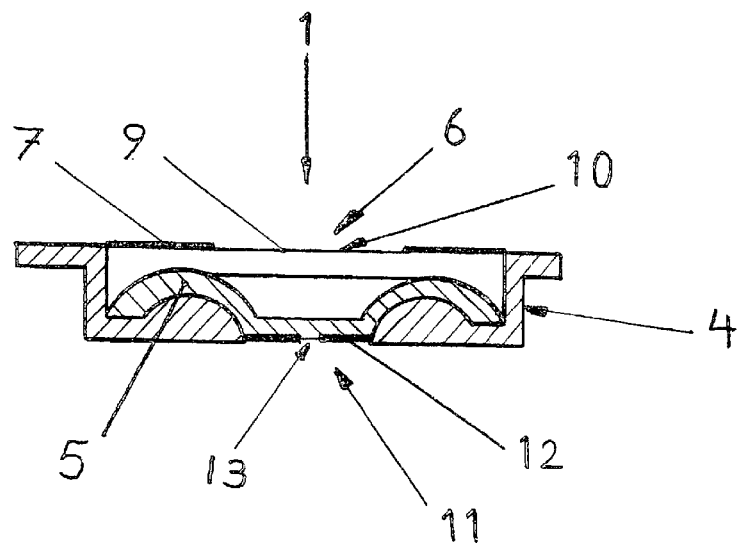
FIG. 4 is a diagrammatic lateral view illustrating an alternative embodiment of a device according to the invention, adapted to apply a coating mass in a pre formed shape.

FIG. 1 shows a preferred embodiment of a disposable device 1 according to the invention and adapted to apply a coating 2 on a tablet, a capsule, a pill or the like 3. The device 1 comprises at least one bowl formation 4 housing a coating mass 5 which can consist of a mixture of ingredients, such as gelatin, glucose, taste- and color-improving substances, and which forms an edible, palatable, preferably elastic and tough material. The top wall or opening 6 of the bowl formation 4 is covered by a foil 7, e. g. made of tinfoil or of a plastic material, which is either detachable or can conveniently be penetrated by the front edge portion 8 of the tablet 3. In order to facilitate a penetration of the foil 7, if it has not been detached, it can be provided with a weakened zone 9 at its central portion 10. The bottom 11 of the bowl formation 4 includes an elastic diaphragm 12 of rubber, plastic or the like, which has a centrally located, easily penetrable opening 13 permitting a tablet 3 to pass and at the same time shaping a thin layer of coating mass 5 on the tablet 3.

In connection with retail sale to consumers a plurality of bowl formations 4, which contain a coating mass 5, may be disposed adjacent each other and held together by cards 14 as shown in FIG. 3.

When a coating mass 5 is to be applied to a tablet 3 one does either first detach the foil 7 or push the tablet 3 through the foil 7 into direct contact with the mass and then out through the opening 13 centrally located in the diaphragm 12. The opening widens and shapes the coating mass 5 to an even coating 2 consisting of a film enclosing all of the tablet. This design makes it possible to apply coatings on tablets of most types and sizes.

In order to cut off the tail of coating mass, which can be formed on a tablet pushed through the device, cutting means, not shown in the drawing, can be disposed adjacent the bottom 11 of each bowl formation 4.

As appears from the above description bowl formations 4 and their content are disposable.

While the present invention has been described in accordance with preferred compositions and embodiments, it is to be understood that certain substitutions and alterations may be made thereto without departing from the spirit and scope of the following claims.

What is claimed is:

1. A method for applying a coating on a tablet, a capsule or a pill, comprising:

providing a device having a bowl formation having a cavity defined therein, a coating mass being disposed in the cavity of the bowl formation, the bowl formation having a bottom with an elastic diaphragm, the diaphragm having a diaphragm opening defined therein;

pushing the tablet, capsule or pill through the coating mass disposed in the bowl formation so that the coating mass encloses the tablet, capsule or pill; and while passing the coated tablet, capsule or pill through the opening of the diaphragm to widen the opening, the diaphragm shaping a film of coating mass on the entire tablet, capsule or pill.

2. A device for coating a tablet, a capsule, or a pill (3) comprising a bowl formation (4) containing a coating mass (5), the bottom (11) of the bowl formation (4) having a diaphragm (12) having a conveniently penetrable opening (13) permitting passage of the tablet (3) and the simultaneous shaping of a thin layer of coating mass (5) on the tablet, capsule or pill, the bowl formation (4) having an upper opening (6) defined therein, a foil (7) covering the upper opening (6).

3. A device according to claim 2 wherein the diaphragm (12) covering the bottom (11) of the bowl formation (4) is elastic.

4. A device according to claim 2 wherein at the bottom (11) of the bowl formation (4) there are cutting means adapted to cut off a tail of coating mass when the tablet, the capsule or the pill has passed through the diaphragm (12).

* * * * *